US006689320B1

(12) United States Patent  
Markart

(10) Patent No.: US 6,689,320 B1  
(45) Date of Patent: *Feb. 10, 2004

(54) TEST STRIP MEASURING SYSTEM

(75) Inventor: Ernst Markart, Munich (DE)

(73) Assignee: LRE Technology Partner GmbH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/378,414

(22) Filed: Aug. 20, 1999

(30) Foreign Application Priority Data

Aug. 20, 1998 (DE) .......................... 298 14 997

(51) Int. Cl.⁷ .............................................. G01N 33/48
(52) U.S. Cl. ......................... 422/68.1; 422/58; 422/61; 422/82.01; 422/82.05; 422/98; 436/165; 436/164; 436/149
(58) Field of Search .................. 422/58, 61, 81, 422/63, 68.1, 82.01, 82.02, 82.05, 82.06, 98; 436/164, 165, 174, 178, 149

(56) References Cited

U.S. PATENT DOCUMENTS 5,281,395 A * 1/1994 Markart et al. .......... 422/82.05
5,405,510 A * 4/1995 Betts et al. .................... 422/58
5,637,275 A * 6/1997 Carey et al. ................... 422/81
5,793,030 A * 8/1998 Kelly, Jr. ..................... 235/385
6,315,951 B1 * 11/2001 Markart ........................ 422/61

* cited by examiner

Primary Examiner—Lyle A. Alexander  
(74) Attorney, Agent, or Firm—McCormick, Paulding & Huber LLP

(57) ABSTRACT

In a test strip measuring system, such as for measuring the concentration of certain substances in body fluids, the system consists of a test strip onto which the fluid to be investigated is applied, and a measuring device into which the test strip is inserted for making the desired measurements. The system further includes a code carrier with a memory storing information concerning the manufacturing of the test strip and/or the measurement to be carried out in using the test strip. Still further, the system includes an adapter through which the code carrier is connectable with a data processing unit for the measuring device. On one hand, the adapter allows one and the same code carrier to be used with different measuring device and on the other hand allows different code carriers to be used with one and the same measuring devices.

16 Claims, 3 Drawing Sheets

TEST STRIP MEASURING SYSTEM

FIELD OF THE INVENTION

The invention concerns a measuring system with a test strip having at least one test field and a measuring device for optically or by means of electrical current measuring the test field, wherein the test strip or a test strip package containing at least one test strip has associated with it a code carrier carrying coded information about the manufacturing of the test strip or about the measurement to be carried out.

BACKGROUND OF THE INVENTION

Measuring systems of the above-mentioned kind are, for example, used for the monitoring of the concentration of certain substances in body fluids, for example, for blood sugar determination. Test strips of different manufacturing batches can have characteristic data differing from one another. Therefore, these characteristic data must be communicated to the measuring device for the carrying out of the measurement. Also, it is possible that such a measuring device is suited for the carrying out of different types of measurements. In this case, the measuring device before the insertion of the test strip must be informed about what measurement the inserted test strip is intended for. Such data are customarily stored in the code carrier.

This invention has as it object the provision of a measuring system of the previously mentioned kind wherein code carriers of different form are couplable with one and the same measuring device or whereby one and the same code carrier is couplable with different measuring devices.

SUMMARY OF THE INVENTION

This object is solved in accordance with the invention by an adapter which is on one hand couplable with the measuring device and on the other hand is connectable with the code carrier. The inventive solution offers the possibility of using code carriers of different kind and shape with one and the same measuring device. While the measuring device has a relatively long useful life, the useful life of the code carrier is generally relatively limited to the time within which a test strip package is used and with which package the code carrier is supplied. The code carriers are, therefore, often changed, and perhaps there exists the possibility of buying another memory chip on the market, or that the manner of storing the coded information may be changed. In all these cases, the adapter need be only suited to the changed code carrier while the measuring device itself remains unchanged. Likewise, there exists the possibility of providing differently shaped adapters for different measuring devices so that one and the same code carrier can find use in different measuring devices.

Preferably, the measuring device has a adapter receiver, which for example can be formed as an insertion chamber or as a plug with at least a portion of the outer contour of the adapter being formed complementary to the shape of the adapter receiver. The adapter receiver and the adapter can, therefore, be related to one another according to a kind of lock and key principle. Preferably, the adapter receiver and the part of the adapter contour which corresponds to it are asymmetrically shaped so that the adapter can be inserted into the adapter recess in only one given way.

In the same way, the adapter can have a carrier recess for the code carrier which is asymmetrically shaped with the outer contour of the code carrier being formed complementary to the carrier recess.

If the code carrier has an electronic memory for storing the coded information or consists of such a memory chip, it is desirable if the adapter has first electric contact elements for electrical connection with the code carrier and second electric contact elements for electrical connection with counter contact elements in the adapter recess, with the first and second contact elements being connected with one another by conductor paths. In this way, the spatial arrangement of the terminals on the code carrier can match a spatial arrangement suited for the electrical connection with the measuring device.

The conductor paths can, for example, consist of conductive adhesive.

According to a preferred embodiment of the invention, the adapter has a transponder-reading unit for the reading of data out of the memory of the code carrier and for transmitting the data to the measuring device. Preferably, in this case, the transponder-reading unit is constructed for the conversion of the data format in which the data is stored in the code carrier to a data format suited for the processing of the data in the measuring device. Therefore, the manufacturer of the code carrier is relatively free to select the style in which the data is stored in the memory of the code carrier. The transponder-reading unit reads the data from the memory and converts it as the case may be into a form suitable for processing in the measuring device.

Further features and advantages of the invention will be apparent from the further dependent claims and the following description which, with reference to the accompanying drawings, explain the invention by way of exemplary embodiments.

DETAILED DESCRIPTION OF THE PREFERRED EMBODIMENTS

Figure 1:
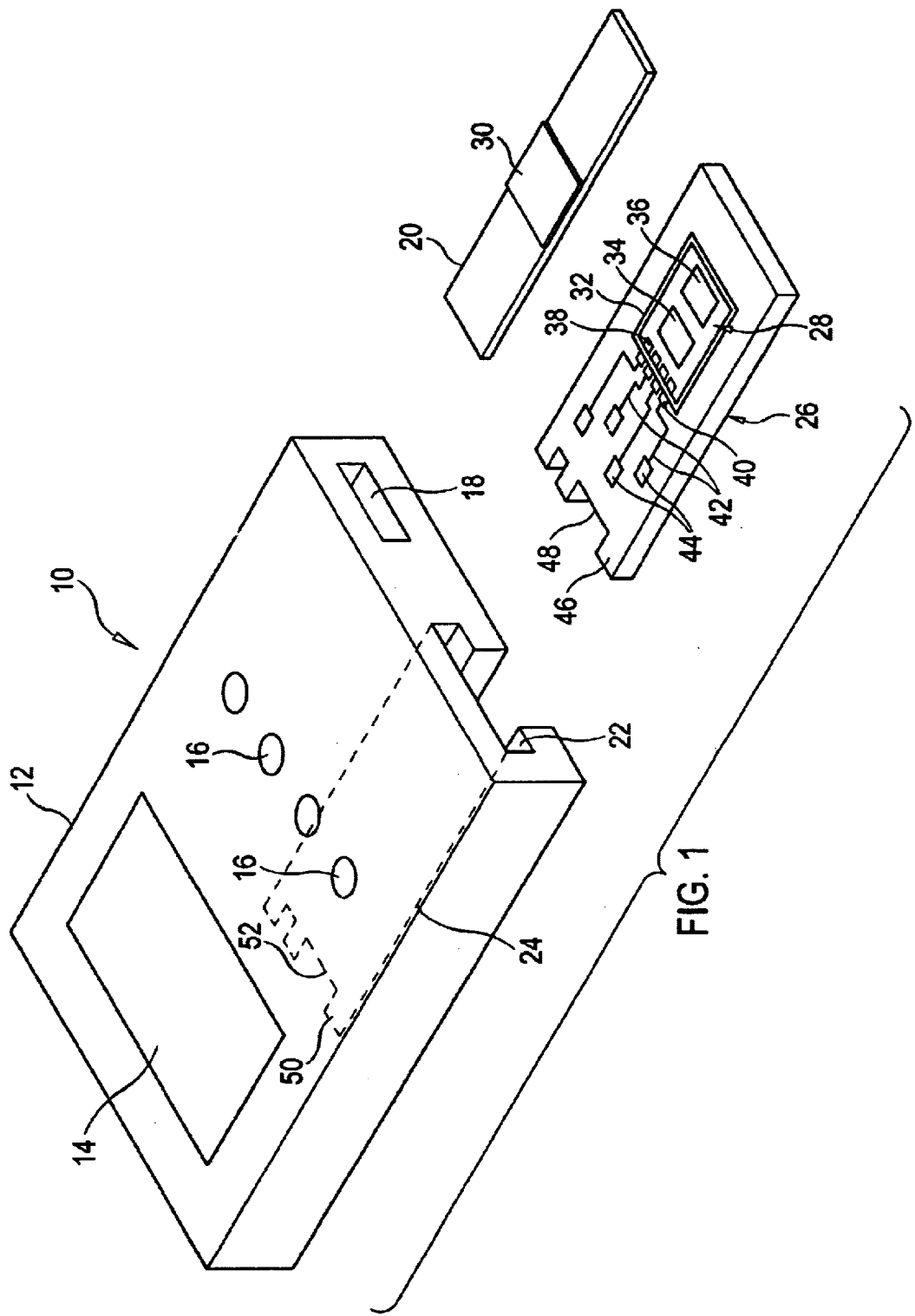
FIG. 1 A schematic illustration of an exemplary embodiment of a measuring system according to the invention with a measuring device, test strip and adapter-code carrier, FIGS. 2–7 schematic sections through different embodiments of an adapter received in the measuring device, FIG. 8 a plan view of a modified form of an adapter with code carrier, and FIG. 9 a section corresponding to that of FIG. 3 through a measuring device, an adapter and a code carrier.

FIG. 1 shows a measuring device, indicated generally at 10, with a housing 12, an indicator mechanism 14 and operating elements 16. The housing 12 has an insertion opening 18 for a test strip 20 as well as a further insertion opening 22 of a receiver 24 for an adapter, indicated generally at 26, which includes a code carrier 28.

The test strip 20 has a test field 30 onto which the fluid to be investigated is dropped. The measuring device 10 includes a measuring device for optically or by means of electrical current measuring the test field 30 to, by way of the measured data, determine for example the concentration of a given substance in the applied liquid. Such measuring methods and test strips are known and need not be explained here in further detail.

The adapter 26 consists of a rectangular part having a receiver 32 for the code carrier 28. The code carrier can, for example, be snapped into the receiver 32 in any desired way. The code carrier 28 contains an electronic group of components which include at least a memory 34 and as the case may be, a data processor 36. The group of components can be unified into an integrated circuit. The code carrier at its edge has contact elements 38 for electrical connection with first contact elements 40 provided on the adapter 26. These first contact elements 40 are connected by conductors 42 with second contact elements 44 on the adapter, the arrangement of which is suited to the arrangement of corresponding counter contact elements (not illustrated) in the adapter receiver 24.

The memory 34 on the code carrier 28 serves to store data which, for example, concerns information about the kind of measurement to be carried out, the characteristic curve of the test strip, or manufacturing data of the test strip. The data processor 36 contains different programs with the help of which the data contained in the memory 30 in coded form can be read out in different ways and can be transmitted to the memory device 10. Which of these programs is activated is determined by control information transmitted from the measuring device 10. This control information can be selected in a previously established way or, according to a random principle. The control information establishes whether the data to be transmitted to the measuring device, for example, is to be negated or non-negated, inverted, mirrored, shifted by a given number of bit positions, coupled in accordance with a given logic, or forwardly or rearwardly or in some other way read out of the memory. Also, by way of the control information, the beginning address of the data to be read out can be given. It is, therefore, not sufficient for a potential counterfeiter of the code carrier to read out and copy the information from the memory 30. This information by itself is worthless, so long as it is not known how the information is to be read. The measuring device itself can read this information only with the help of the data processor 32 whose internal reading program can be so secreted so that it can, if at all, only be determined at considerable expense.

The forward edge of the adapter 26 facing the measuring device is provided with projections 46 and recesses 48. These projections and recesses correspond to complementary recesses 50 and projections 52 in the adapter receiver 24. The projections and recesses 46, 48, therefore, interdigitate with the recesses 50 and the projections 52 according to the key and lock principle. In a similar way, the contact elements 44 cooperate with the corresponding counter contact elements in the measuring device 10. Thereby it is assured that only the correct adapter can be so inserted into the measuring device 10 so as to make possible a communication between the code carrier and the measuring device.

Figure 2:
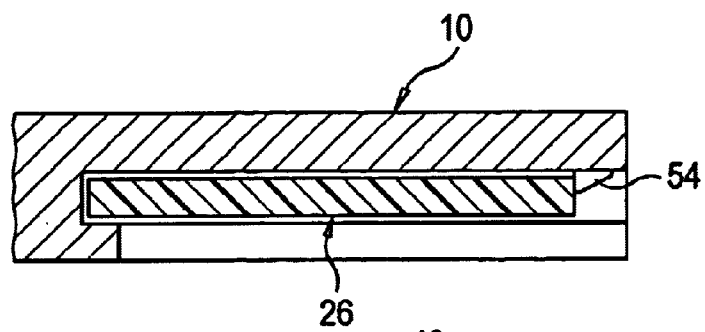

FIG. 2 shows in schematic way the adapter 26 inserted in the adapter recess 24 of the measuring device 10, which adapter is fixedly held in its inserted position by way of a catchnose 54. Usually, one will want to be able to again remove the adapter 26 from the adapter receiver 24. For this purpose, in the illustrated embodiment of FIG. 3 a spring 56 is so movably supported on the measuring device 10 that by depressing the actuating portion 58 of this spring the adapter 26 can be pressed downwardly so that it will move free of the catchnose 54. The embodiment illustrated in FIG. 4 has the same effect, and in this embodiment, instead of the illustrated curved leaf spring 56 of FIG. 3, a pressure key 60 is provided by means of which the adapter 26 can be pushed downwardly out of its locked position.

Figure 5:
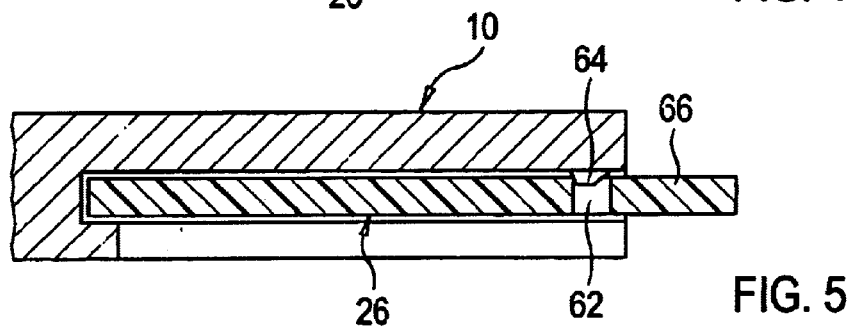

In the embodiment illustrated in FIG. 5, the adapter 26 has a recess 62 into which a spring element 64 snaps after the insertion of the adapter 26 into the adapter recess 24, the spring element 64 being arranged on the upper side of the adapter recess 24. By pulling on the grip end 66 of the adapter 26, the detent resistance of the catch element 64 can be overcome and thereby the adapter 26 can again be withdrawn from the adapter recess 24.

Figure 6:
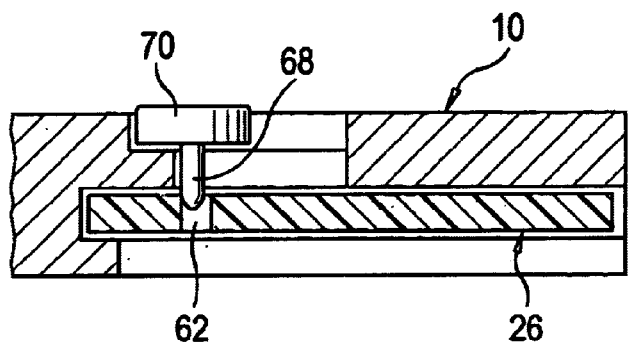

FIG. 6 shows an embodiment in which the adapter 26 likewise has a recess 62 which can be brought into releasable holding engagement with a projection 68 on a sliding key 70, which key is slidably guided in the measuring device 10 and with the help of which the adapter 26 can again be pushed out of the recess 24.

Figure 7:
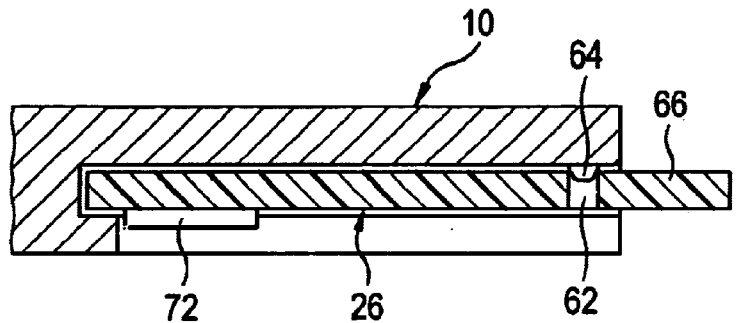

FIG. 7 lastly shows an embodiment in which the adapter 26 carries a transponder-reading unit 72 which lies in a free recess of the measuring device. This embodiment is suited for use with code carriers which have only a data memory 34 and which do not have a data processor 36. The transponder-reading unit reads the data out of the memory 34 and converts it as the case may be to a format suited for the processing carried out in the measuring device. The adapter has, in respect to data technique, the function of an interface. The arrangement of the transponder-reading unit is suited for an inductive coupling.

Figure 3:
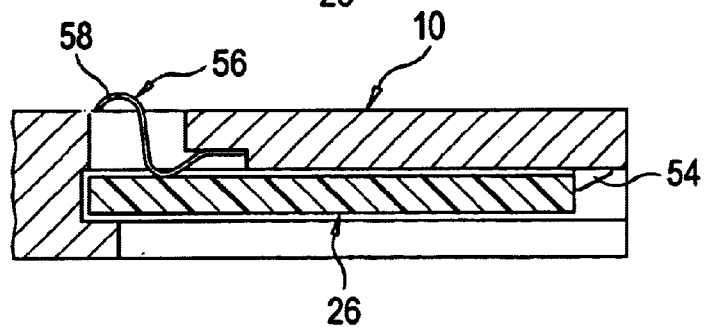
Figure 4:
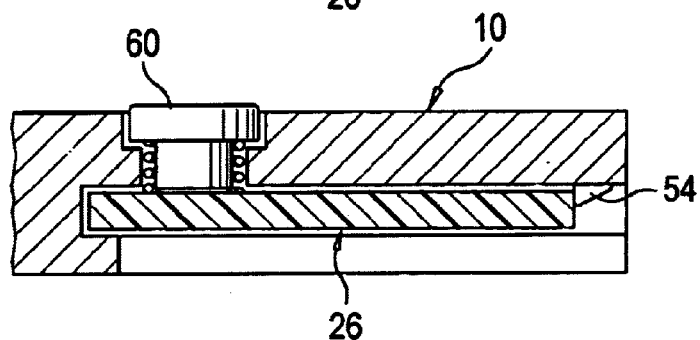
Figure 8:
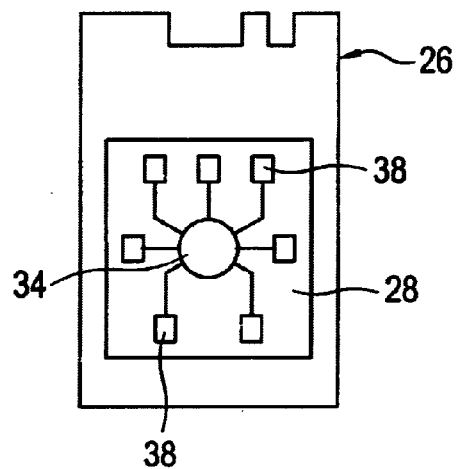
Figure 9:
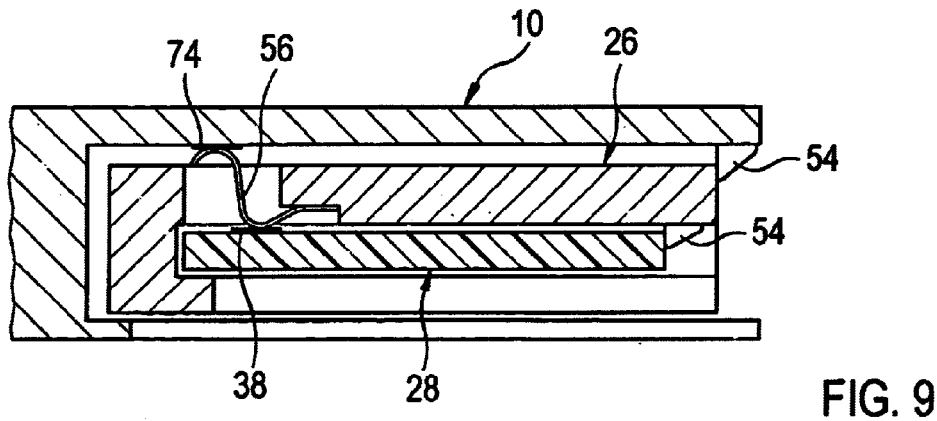

FIG. 8 shows a modified embodiment of the adapter 26 with a code carrier 28 wherein the contact elements 40 and 44 on the adapter 26 are omitted and the code carrier has a memory 34 connected with contact elements 38 which are directly connectable with the measuring device 10. This, for example, can occur in the form illustrated in FIG. 9 which shows a view similar to that of FIG. 3, with the part in FIG. 3 representing the measuring device 10 now forming the adapter and the part of FIG. 3 forming the adapter 26 now representing the code carrier. Both parts are inserted into the adapter recess of the measuring device 10. The leaf springs illustrated in FIG. 3 are here fastened to the adapter 26 and form at the same time contact elements which connect the contact elements 38 on the code carrier 28 with counter contact elements 74 on the measuring device.

Moreover, the representations of FIGS. 2–6, in which detent holdings of the adapter 26 in the adapter receiver 24 of the measuring device 10 are shown are also capable of being used with the arrangement of the code carrier 28 in the carrier recess 22 of the adapter 26. That is, the reference numerals 10, 24 and 26 in FIGS. 2–6 can be replaced by the reference numerals 26, 32 and 28.

What is claimed is:

1. A measuring system with a test strip (20) having at least one test field (30), and a measuring device (10) for optically or by means of electric current measuring the test field (30), with a code carrier (28) materially separate from the test strip (20), which code carrier (28) carries coded information concerning the manufacturing of the test strip (20) or the measurement to be carried out in connection with the test strip, characterized by an adapter (26) couplable with the measuring device (10) and connectable with the code carrier (28) so that the adapter (26) releasably holds the code carrier (28), by the measuring device (10) having a first opening including an adapter recess (24) for receiving and releasably retaining the adapter (26) while the code carrier (28) is held on the adapter (26), by the measuring device (10) having a second opening including a strip insertion opening (18) for receiving the test strip, and by the measuring device (10) being adapted both to read the code carrier (28) when the adapter (20) with the code carrier held thereon is in the adapter recess (24) and to read the test strip (20) when the test strip is in the test strip insertion opening (18).

2. A measuring system according to claim 1, further characterized in that at least a portion of the outer contour (46, 48) of the adapter is formed complementary to the shape of the adapter recess (24).

3. A measuring system according to claim 2, further characterized in that the adapter recess and the portion of the adapter contour which corresponds to it are formed asymmetrically.

4. A measuring system according to claim 2, further characterized in that the adapter has a carrier recess (32) for the code carrier (28), which carrier recess (32) is shaped asymmetrically, and in that the outer contour of the code carrier (28) is formed complementary to the carrier recess (32).

5. A measuring system according to claim 2, further characterized in that the code carrier (22) has an electronic memory (32) for storing the coded information and in that the adapter (26) has first electric contacts (40) for electrical connection with the code carrier (28) and second electric contacts (44) for electrical connection with counter contact elements in the adapter recess (22), with the first and second contacts (40, 42) being connected with one another by conductor paths (42).

6. A measuring system according to claim 5, further characterized in that the conductor paths (42) are made of conductive adhesive.

7. A measuring system according to claim 2, further characterized in that the adapter (26) is releasably snappable into the adapter recess (24).

8. A measuring system according to claim 2, further characterized in that the code carrier (28) is releasably snappable into the carrier recess (32).

9. A measuring system according to claim 1, further characterized in that the adapter (26) has a transponder-reading unit (22) for reading out data from the memory (24) of the code carrier (28) and for transmitting the data to the measuring device (10).

10. A measuring system according to claim 9, further characterized in that the transponder-reading unit (72) converts the data format in which the data is stored in the code carrier (28) to a data format suitable for the processing of the data in the measuring device (10).

11. A measuring system according to claim 7, further characterized in that the adapter (26) with the help of detent springs (56) is snappable, into the adapter recess (24), with the detent springs (56) being fastened to the adapter (26) and being formed for making an electrical connection of the contacts (38) of the code carrier (28) with the contacts (74) of the measuring device (10).

12. A measuring system according to claim 7, further characterized in that the adapter (26) is snappable, into the adapter recess (24) and/or the code carrier (28) is snappable into the carrier recess (32) by means of a detent nose (54).

13. A measuring system according to claim 7, further characterized in that the adapter (26) is lockable into the adapter recess (24) and/or the code carrier (28) is lockable into the carrier recess (32) by means of a detent element receivable in a recess (62) in the adapter (26) or in the code carrier (28).

14. A measuring system according to claim 7, further characterized in that the adapter (26) and/or the code carrier (28) is unlockable by a pressure key (80) supported in the measuring device or in the adapter (26).

15. A measuring system according to claim 7, further characterized in that the adapter (26) and/or the code carrier (28) is unlockable by a slide (70) supported in the measuring device (10) or in the adapter (26).

16. A measuring system according to claim 10, further characterized in that the transponder-reading unit (72) lies in a free recess of the measuring device (10).

* * * * *